United States Patent [19]

Teder

[11] Patent Number: 5,661,303
[45] Date of Patent: Aug. 26, 1997

[54] COMPACT MOISTURE SENSOR WITH COLLIMATOR LENSES AND PRISMATIC COUPLER

[75] Inventor: Rein S. Teder, Bloomington, Minn.

[73] Assignee: Libbey-Owens-Ford Co., Toledo, Ohio

[21] Appl. No.: 653,546

[22] Filed: May 24, 1996

[51] Int. Cl.[6] ................................................. G01N 21/17
[52] U.S. Cl. ........................... 250/341.8; 250/227.25
[58] Field of Search ........................ 250/341.8, 227.25; 356/445

[56] References Cited

U.S. PATENT DOCUMENTS

| | | | |
|---|---|---|---|
| 3,947,131 | 3/1976 | Karl | 356/445 |
| 4,652,745 | 3/1987 | Zanardelli | 250/227.25 |
| 5,414,257 | 5/1995 | Stanton | 250/341.8 |

*Primary Examiner*—Michael J. Tokar
*Assistant Examiner*—Richard Hanig
*Attorney, Agent, or Firm*—Marshall & Melhorn

[57] ABSTRACT

A compact rain sensor for mounting on the inner surface of a windshield includes collimator lenses and a detachable prismatic coupler to facilitate the mounting of emitters and detectors on a circuit board which is positioned parallel to the inner surface of the windshield. A thin optical coupler is adhesively secured to the windshield. A sensor housing is detachably secured about the outer edges of the coupler. Within the sensor housing, surface-mounted infrared emitters and detectors, as well as signal processing circuitry, are all mounted on a single printed circuit board secured in the housing. When the sensor housing is mounted on the coupler, the printed circuit board is parallel to the inner surface of the windshield and in close proximity thereto. In operation, a light beam from the emitter enters the windshield at a forty-five degree angle and is reflected back from the outer surface of the windshield to the detector, which generates a control signal based on the amount of light reflected from the outer surface. Moisture on the outer surface of the windshield reduces the amount of light reflected to the detector. Surface mounted emitters and detectors, which are very cost and space efficient, are mounted on the circuit board with an initial optical axis perpendicular to the circuit board. In order to achieve the desired forty-five degree angle of entry into the windshield, the light beam emitted from the emitter is reflected, refracted, and collimated prior to entry into the windshield by collimator lenses mounted on the circuit board and by prismatic regions formed in the coupler.

20 Claims, 4 Drawing Sheets

COMPACT MOISTURE SENSOR WITH COLLIMATOR LENSES AND PRISMATIC COUPLER

BACKGROUND OF THE INVENTION

1. Field of the Invention

The present invention relates generally to an optical moisture sensor for mounting upon the interior surface of a windshield, and more particularly, to a compact optical moisture sensor having a optical emitters, detectors, and optical components mounted on a planar circuit board which is positioned parallel to the interior surface. Collimator lenses and a prismatic coupler are used to reflect and refract light beams as the light beams travel from the emitters to the outer surface of the windshield and back to the detectors.

2. Summary of Related Art

Motor vehicles have long been equipped with motor-driven windshield wipers for cleaning moisture from the external surface of the windshield, at least within the driver's field of vision, and generally over a larger area so as to enhance vision through the windshield. In most vehicles today, the windshield wiper system includes multi-position or variable speed switches which allow the driver to select a wide, if not an infinitely variable, range of speeds to suit conditions. Wiper controls are manually operated and typically include a delay feature whereby the wipers operate intermittently at selected time delay intervals.

Wiper control systems have recently been developed which include a moisture sensor mounted on the windshield to automatically activate the motor when moisture is deposited upon the surface of the windshield or other vehicle window upon which a wiper may be employed, such as the rear window. By sensing rain or other moisture on the glass surface, the wipers can be controlled accordingly. Such wiper control systems free the driver from the inconvenience of frequently adjusting the wiper speed as the driving conditions change. Wiper control systems with optical moisture sensors have been incorporated into the production of several models of passenger cars. In order to increase the commercial use and consumer acceptance of the wiper control systems, there is a need for a more compact and less expensive optical moisture sensor.

Wiper control systems have employed a number of different technologies to sense the moisture conditions encountered by a vehicle, including conductive, capacitive, piezoelectric, and optical sensors. Optical sensors operate upon the principle that a light beam being diffused or deflected from its normal path by the presence of moisture on the exterior surface of the windshield. The systems which employ optical sensors have the singular advantage that the means of sensing (i.e. disturbances in an optical path) is directly related to the phenomena observed by the driver (i.e., disturbances in the optical path that affords the driver vision). Thus, optical systems generally have an advantage over other sensor technologies in that they are closely related to the problem corrected by the wipers.

McCumber et al. (U.S. Pat. No. 4,620,141) disclose an automatic control circuit for triggering a sweep of the wiper blades in response to the presence of water droplets on the exterior surface of a windshield. The rain sensor devices for controlling the windshield wipers of a vehicle as disclosed by McCumber et al. and Teder (U.S. Pat. Nos. 5,059,877 and 5,239,244) include a box-like housing mounted upon the interior surface of the windshield. The presence of moisture on the surface of the windshield affects the reflection of light at the air-glass interface, and this change in reflected light is electronically processed and utilized as the signal for activating the windshield wipers. The sensor housing in an optical moisture sensor should securely engage the windshield and be optically coupled to the windshield so as to effectively eliminate the interface between the light emitters-detectors and glass surface from an optical standpoint. U.S. Pat. No. 5,262,640 to Purvis et al. describes an intermediate adhesive interlayer for affixing the sensor housing to the windshield. The sensor housing is affixed directly to the surface of the windshield or other vehicle window by means of an intermediate interlayer disposed between the sensor housing and the interior surface of the windshield.

In optical moisture sensors, light from an emitter is directed by a guide means into the windshield at an angle of approximately forty-five degrees with respect to the windshield. The light is then reflected by the outer surface of the windshield at approximately a forty-five degree angle and is directed by a guide means into a detector. Water on the outside surface of the windshield effects the overall transmittance of the optical path between emitter and detector.

When the angle of entry of the light beam into the windshield is greater than fifty degrees, a loss of signal frequently occurs. When the angle of entry is less than forty degrees, a loss of sensitivity occurs and the sensor is not able to properly detect moisture on the windshield. Consequently, it is essential that the angle of entry of the light beam from the emitter enter the windshield at approximately forty-five degrees.

The desired forty-five degree angle can be achieved by mounting the optoelectronic devices (emitters and detectors) at forty-five degree angles or by deflecting the light as it travels between the devices and the glass windshield. The sensors in which the emitters and detectors are mounted at forty-five degree angles to the windshield have required bulky, box-like enclosures. Light may be deflected only by reflection, refraction or diffraction. Reflecting mirrors are amenable to deflections of sixty degrees or greater. A mirror designed to implement a shallower deflection must be quite large to accommodate a wide splay of rays. Diffractive lenses are not very efficient and can be quite expensive. A refractive service can efficiently deflect a beam approximately twenty degrees or less. The preferred forty-five degree angle for optical moisture sensors is generally too small for a reflective system and too large for a refractive system. Consequently, most of the optical sensors have used optical devices deployed at a suitable angle rather than devices for deflecting the light at the desired angle.

The references cited above have optical devices deployed at forty-five degrees, which requires a box like enclosure. Additional examples of optical sensor mounting configurations to achieve the forty-five degree angle between the optical axis of the emitter and the glass windshield are disclosed in Noack (U.S. Pat. No. 4,355,271), Bendicks (U.S. Pat. No. 5,323,637) and Larson (U.S. Pat. No. 4,859,867).

Stanton (U.S. Pat. No. 5,414,257) discloses optical sensor optoelectronic devices mounted on a circuit board at an appropriate angle to change or deflect the optical axis. Stanton teaches devices cast from flexible epoxy resin and the bending of the leads to the desired angle. The problem with electronic devices with bent leads is that most automated component insertion equipment cannot insert components with bent leads. In addition to increased costs to assemble the circuit boards, the bent lead devices are less reliable from a performance standpoint.

The mounting of optoelectronic devices on circuit boards is also disclosed in Schierbeek (U.S. Pat. No. 4,956,591) and in Wiegleb et al. (DE3806881). The optoelectronic devices are mounted on small circuit boards which are aligned perpendicular to the windshield. Reflective surfaces, each bending the light ninety degrees in a rotational fashion, deflect the optical axis to the required angle within the windshield. Although the mounting configurations in these references do not require lead forming, the use of such small circuit boards creates other problems. The small circuit boards used to mount the optoelectronic devices cannot accommodate the signal processing circuitry, which must be located on a separate circuit board. The use of multiple circuit boards and the orientation of the circuit boards in the housing of the sensor increases the size and cost of the sensor. The required mounting angles for the optoelectronics in a sensor could also be obtained by the use of flexible circuit boards, but such material is more expensive and less reliable than standard circuit boards.

Optoelectronic devices are customarily mounted and aligned on a printed circuit board, which also accommodates signal processing. Conventional optoelectronic devices, including the new surface-mount technology devices (SMT's), are generally designed so that their optical axis is normal to the circuit board on which they are mounted. The use of a single circuit board mounted coplanar with the surface of the windshield could result in a low cost and compact sensor enclosure. However, such design presents significant problems in achieving the desired forty-five degree configuration because the optical axis is perpendicular to the circuit board.

One configuration which both reduces the cost and reduces the size of the optical sensor is to use a single detector to simultaneously detect two or more emitters, as disclosed in Noack. Such a configuration provides the desired area of detection with a fewer number of detectors. However, the light paths are widely splayed, which requires a larger detector or additional optical elements for concentrating the light.

Another area of concern in the manufacture of optical moisture sensors is the mounting of the sensor to the windshield. Vehicle manufactures desire a sensor which is already installed at the windshield manufacturer, or a sensor that is very easy to install on the vehicle production line. The windshield manufacturer ships windshield nested together such that there is very little spacing for mounting a sensor.

Schofield (U.S. Pat. No. 4,930,742) discloses the use of a bracket, such as a rear view mirror bracket, for mounting the optical moisture sensor. This approach necessitates additional support structure or the addition of silicone pieces to optically couple the moisture sensor to the windshield. A bracket mounting systems results in additional parts and increased costs.

Bendix (U.S. Pat. No. 5,278,425) and Stanton teach that a lens may be permanently affixed to the windshield such that a sensor housing may be detachably mounted on the lens. The lens may impart focal power to the beam, as in shown Bendix. Alternatively, the lens may couple the beams to the windshield through planar surfaces normal to the beam direction, as disclosed in Stanton. However, both Bendix and Stanton require a lens that is approximately as thick as the windshield. When stacking the windshields for transportation from the glass manufacturer to the vehicle assembly line, the additional space necessitated for the lens adds additional handling costs to the cost of the windshield.

Watanabe (U.S. Pat. No. 4,701,613) discloses an integral coupler lens having a series of V-grooves forming a segmented prism with planar surfaces normal to the direction of the beams. Segmented lenses have a greater potential for parasitically admitting ambient light, which reduces optical efficiency and degrades the signal from the emitter. The resulting beam travels at a forty-five degree angle with respect to the windshield, and thus is not amenable to coplanar approaches.

SUMMARY OF THE INVENTION

In accordance with the present invention, there is provided a compact rain sensor for mounting on the inner surface of a windshield. The rain sensor includes collimator lenses and a detachable prismatic coupler to facilitate the mounting of emitters and detectors on a circuit board which is positioned parallel to the inner surface of the windshield.

The thin and lightweight coupler of the present invention is adhesively secured to the windshield. A sensor housing is detachably secured about the outer edges of the coupler. Within the sensor housing, surface-mounted infrared emitters and detectors, as well as signal processing circuitry, are all mounted on a single printed circuit board secured in the housing. When the sensor housing is mounted on the coupler, the printed circuit board is parallel to the inner surface of the windshield. Surface mounted emitters and detectors, which are very cost and space efficient, are mounted on the circuit board with an initial optical axis perpendicular to the circuit board.

Compact collimator lenses performs three optical functions in directing the infrared light beams from the emitters to the prismatic coupler. For each lens, the first surface gathers the light beam and a second surface reflects the light beam such that the optical axis, after starting out perpendicular to the circuit board, is reflected approximately sixty degrees from the initial optical axis. A third surface of the lens forms a convex lens to collimate the rays of the light beam.

After the light beam exits the collimator lens, the light beam enters the prismatic coupler such that the light beam is refracted approximately fifteen degrees in the direction of the initial optical axis and is optically coupled to the windshield. The resulting collimated light beam is traveling at approximately a forty-five degree angle with respect to the circuit board and with respect to the initial optical axis perpendicular to the circuit board. The inner surface of the windshield, which is parallel to the circuit board, receives the rays of the light beam at the desired forty-five degree angle.

The light beam is reflected off of the outer surface of the windshield and back through the windshield at approximately a forty-five degree angle to the prismatic coupler and collimator lens to a detector. Any water present on the outer surface of the windshield effects the amount of light directed back to the detector. The light beam is refracted approximately fifteen degrees by the coupler and is reflected approximately sixty degrees by the collimator lens such that the vertical axis is perpendicular to the circuit board as the light beam is detected by the detector.

In a windshield application, the sensor may be provided with multiple emitter-detector optical systems to provide an array of sensed areas. The emitters and detectors are electrically connected to the windshield wiper control circuitry to control operation of the wiper system.

An object of the present invention is to reduce to size of the sensor, especially the height of the sensor housing extending from the inner surface of the windshield. The combination of beam deflections by reflection and refraction permits the use of surface mounted emitters and detectors on a single circuit board which is parallel to the inner surface of the windshield. With the use of the surface mounted emitters and detectors, the space between the circuit board and prismatic coupler need only be tall enough to accommodate the collimator lenses. The surface of the single circuit board required in the present invention is mounted in close proximity to the inner surface of the sensor housing. The deflection of the light beams into and out of the coupler permits a thin coupler to be used. By mounting all of the components and control circuits on a single circuit board and by mounting such circuit board parallel to the inner surface of the windshield, a significant reduction in the height of the sensor housing can be achieved.

Another object of the present invention is to provide glass manufacturers and motor vehicle manufacturers with a more efficient and cost effective means for mounting the rain sensors on the windshield of a vehicle. In the present invention, the coupler will generally be mounted on the inner surface of the windshields by the glass manufacturer prior to transporting the windshields to the vehicle manufacturing plant. The vehicle manufacturer conveniently mounts the sensor housing, which includes the circuit board, onto the coupler as the vehicle is being assembled. Because the coupler is small, thin, and relatively inexpensive, the coupler can be mounted on all of the windshields being transported from the glass manufacturer to a specific assembly line at an automotive plant without changing the conventional packaging materials used by the glass manufacturer. As the windshields are installed in a vehicle, the mounting of the sensor can be completed by conveniently attaching the sensor housing to the coupler.

A further object of the present invention is to reduce the cost of manufacturing the sensor by mounting all of the optoelectronic components and signal processing circuitry on a single, planar circuit board. The surface mounted technology and chip-on-board technology combined with automated assembly techniques for production of the circuit board provide an improved efficiency and cost reductions in the manufacture of the sensors. The configuration of the present invention eliminates the use of multiple circuit board and lead formation on the optical devices.

An object of the present invention is to provide a moisture sensor having high optical efficiency and improved signal strength. The present invention utilizes single surface lenses, which are more efficient than segmented lenses.

In an alternative embodiment, the collimated light beams from two infrared emitters are directed onto a single detector. An object of the present invention is to reduce the number of required optoelectronic components without increasing the size or reducing the effectiveness and efficiency of the moisture sensor.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
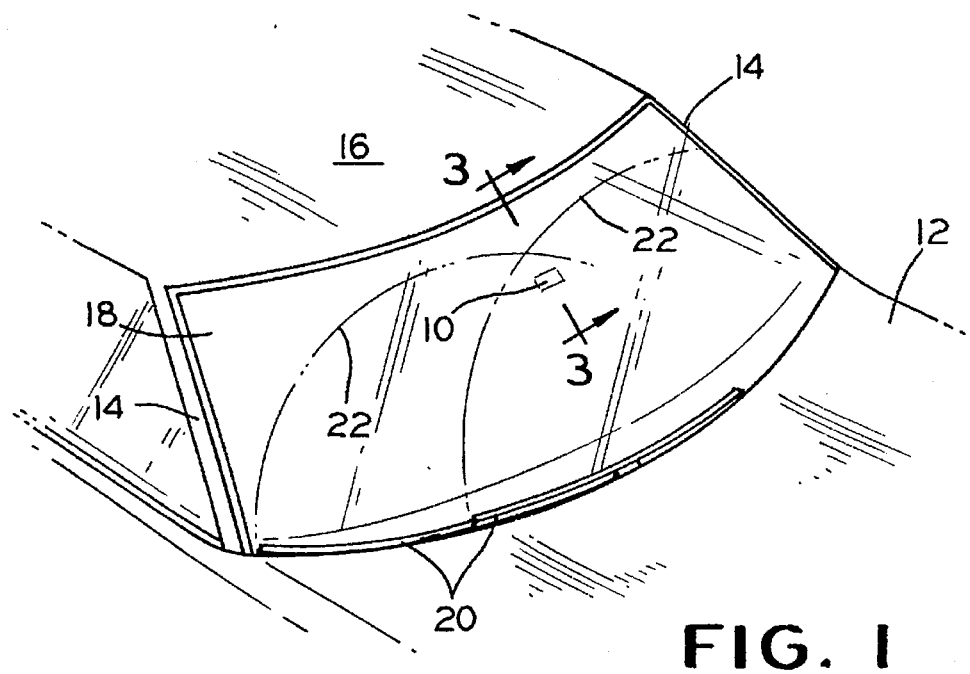
FIG. 1 is a fragmentary perspective view showing an optical moisture sensor mounted upon the windshield of an automobile.

Referring now to FIG. 1, there is shown generally a moisture sensor 10 of the present invention and a portion of an automobile, including a hood 12, side posts 14 and a roof 16 defining an opening within which a windshield 18 is mounted. Windshield wiper blades 20, shown in their at-rest position along the lower edges of the windshield, are operable in a conventional manner to swing in arcs 22 and sweep accumulated moisture from the surface of the windshield 18.

Figure 2:
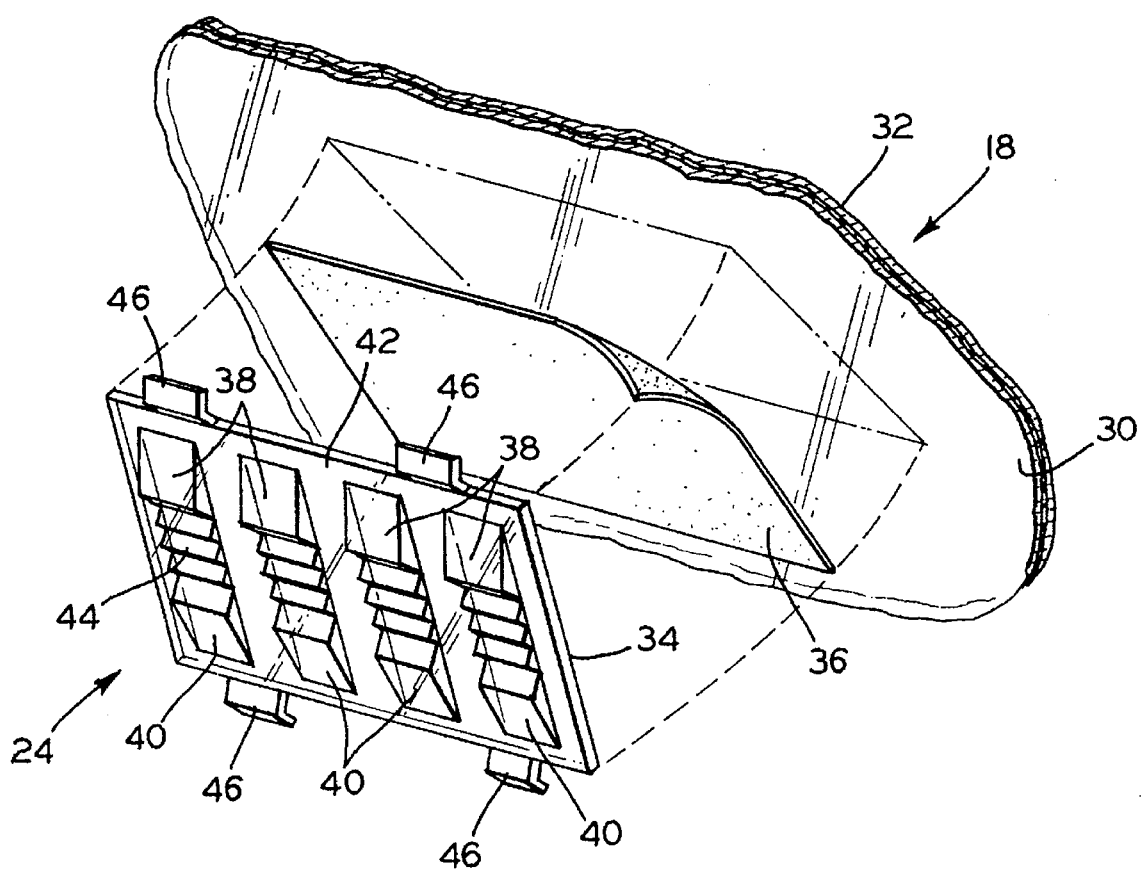
FIG. 2 is an enlarged perspective view showing the mounting of the prismatic coupler with an adhesive interlayer on the inner surface of the windshield.
Figure 3:
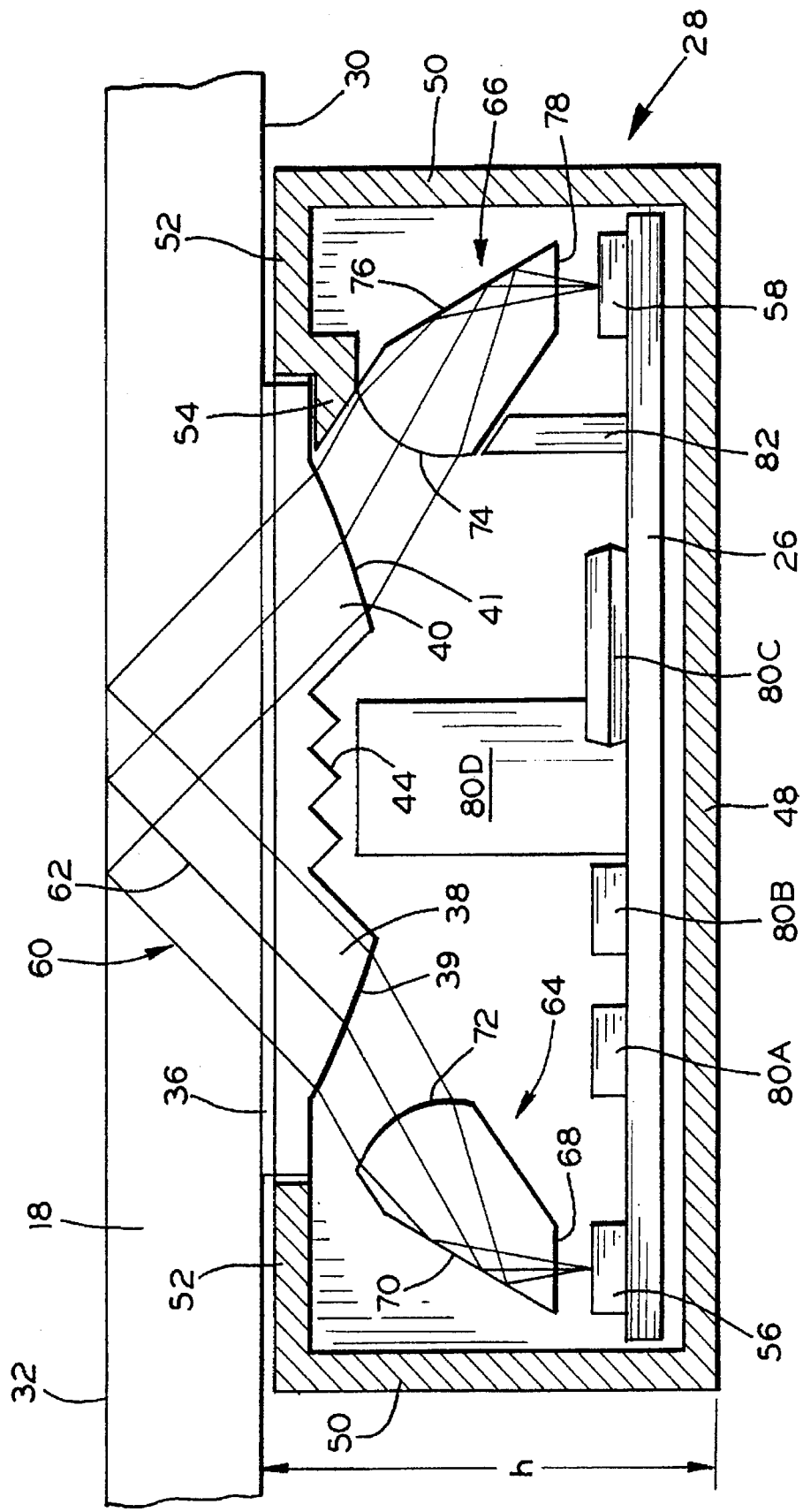
FIG. 3 is a transverse section of the optical moisture sensor showing the sensor mounted on the windshield, taken substantially along line 3—3 of FIG. 1.

As shown in FIGS. 2–3, the moisture sensor 10 includes a prismatic coupler 24, a circuit board 26 for mounting the optoelectronic components and the signal processing circuitry, and a sensor housing 28 for enclosing the circuit board 26 and attachment to the coupler 24.

The coupler 24 is secured to the inner surface 30 of windshield 18 for the optical detection of moisture on the outer surface 32 of the windshield. The moisture sensor 10 is typically mounted adjacent to the rear view mirror on the inner surface 30 so as to minimize any view obstruction for the passengers in the automobile. The windshield 18 is generally relatively flat in the area where the sensor 10 is to be mounted, so that the bottom surface 34 of the coupler 24 may be planar. However, it is contemplated that the bottom surface 34 of the coupler 24 may be correspondingly contoured to match a curved windshield surface where appropriate. A double-sided adhesive interlayer 36 is used to secure the coupler 24 to the windshield 18. The interlayer 36 is made from silicone or other similar flexible plastic material. The coupler 24 may be secured to the windshield 18 by the glass manufacturer prior to transporting the windshield 18 to the automotive assembly line.

The prismatic coupler 24 is made from polycarbonate or other similar material for optically coupling the moisture sensor 10 to the windshield 18. From a material composition standpoint, the coupler 24 must be able to withstand a wide range of temperature to which an automobile may be subjected.

The prismatic coupler 24 shown in FIG. 2 includes four pairs of prismatic regions formed on a base 42, each pair having an emitter prism 38 and a detector prism 40. The emitter prism 38 includes a surface 39 for receiving light beams and the detector prism 40 has a corresponding surface 41 where light beams exit the detector prism 40. The surfaces 39,41 have a light convex curvature and are formed at an angle of approximately twenty-one degrees with respect to the base 42 of the coupler 24. Blocking grooves 44 are formed on the base 42 between the prism pairs 38,40. A plurality of mounting clips 46 are also provided around the periphery of the base 42 for securing the sensor housing 28 to the base 42 of the coupler 24.

The thickness of the prismatic coupler 24 is an important consideration from a packing standpoint when transporting the windshield from the glass manufacturer to the automotive assembly line. Special racks and packaging material have been designed to pack the individual windshields as close as possible for shipping efficiency while protecting the windshields during transport to prevent scratching or other damage to the windshields. The automotive windshields typically include a mounting button on the windshield for mounting the rear view mirror such that the shipping racks can accommodate such mounting button. The prismatic coupler 24 of the present invention is less than 5 mm, which is thinner than the typical mirror mounting button thin. Consequently, the thin prismatic coupler 24 permits the glass manufacturer to mount the coupler 24 on the windshield production line without having to change the packaging and material handling processes used to deliver the windshields to the automobile assembly line. The ability to mount the coupler at the windshield production operations without changing the packaging and material handling features is an important consideration in gaining increased usage of the moisture sensor and wiper control system by the automotive companies.

The circuit board 26 is mounted on the base 48 of the sensor housing 28, as shown in FIG. 3. The sensor housing 28 is made from a hard plastic or other rigid material and includes four vertical walls 50 extending from the base 48. One of the objects of the present invention is to minimize the size of the sensor housing, and specifically, the height (h) of the walls 50 extending from the inner surface 30 of the windshield 18. The walls 50 of the housing 28 include a flange 52 to facilitate retention of the housing 28 by the clips 46 on the base 42 of the coupler 24. The flange 52 of wall 50 adjacent the detector prisms 40 is provided with a blocking edge 54 to block out ambient light from the detectors on circuit board 26.

The present invention includes a single, planar circuit board 26 with the optoelectronic components and signal processing circuitry mounted on the circuit board 26. Conventional surface mounting techniques may be used to mount the components on the circuit board 26. The coupler 24 in FIG. 2 includes prismatic regions for four emitter detector pairs. A system with four emitters provides sufficient area for detection of moisture on the windshield, which results in smooth wiper system performance. However, the techniques of the invention may be applied to other moisture sensing operation and may include any number of emitter and detector pairs.

Referring now to FIG. 3, the cross sectional view of the sensor shows a single emitter 56 and detector 58 pair. Additional emitter 56 and detector 58 pairs may be mounted on the circuit board 26 in a similar manner. The optical path of the collimated light beam 60 as the rays of the light beam 60 travel from the emitter 56 to the outer surface 32 of the windshield 18 and back to the detector 58 is also shown in FIG. 3.

The emitter 56 and detector 58 are surface mounted devices, such as Siemens part numbers SFH-421 and BPW-34FAS, respectively. The detector 58 may be a large photodiode or a phototransistor. The emitter 56 and detector 58 may also be implemented using silicon die bonded directly to the circuit board 26 in a chip-on-board approach. The emitter 56 radiates infrared energy such that a light beam 60 is emitted primarily in a direction that is perpendicular to the surface of the circuit board 26. The optical axis 62 of light beam 60 is normal to the circuit board 26 upon leaving the emitter 56. The optical axis 62 of light beam 60 travels through the nominal center of the optical surfaces in the moisture sensor 10. The detector 58 is mounted so that the axis of highest sensitivity is perpendicular to the circuit board 26. The detector 58 also has an angle of acceptance such that light beams striking the detector along the perpendicular axis of highest sensitivity or within the angle of acceptance about such axis will cause the detector 58 to generate a control signal.

A collimator lens 64 is mounted adjacent the emitter 56 and centered along the optical axis 62 of light beam 60. A similar collimator lens 66 is mounted adjacent the detector 58. Mounting posts (not shown) are used to support and position the collimator lenses 64,66 on the circuit board 26. The collimator lens 64 includes a planar surface 68, which reduces the divergence of the rays of the light beam 60. The mirror surface 70 of the lens 64 acts as a folding mirror to reflect the light beam 60. The mirror surface 70 is positioned at an angle of sixty degrees with respect to the surface of the circuit board 26. When light beam 60 strikes the mirror surface 70, the light beam 60 is reflected by the process of total internal reflection such that the optical axis is reflected approximately sixty degrees from its initial path perpendicular to the circuit board 26. The collimator lens 64 also includes a convex lens surface 72 at the end of the lens 64. The convex lens surface 72 decreases the divergence of the rays of the light beam 60 to that of an almost collimated condition as the light beam 60 exits the collimator lens 64.

The collimator lens 66 adjacent the detector 58 also has a convex lens surface 74, a mirror surface 76, and a planar surface 78 for reflecting the light beam 60 to the detector 58. The optical axis 62 of the light beam 60 is reflected such that the path of the light beam 60 is changed by approximately sixty degrees to achieve the desired perpendicular angle of entry of the light beam 60 into the detector 58. Although the preferred angle at the detector is perpendicular, any light beams 60 within the angle of acceptance will be detected by the detector 58. The angle of acceptance for surface mounted detectors is generally in the thirty to sixty degree range.

The signal processing circuitry includes conventional components 80A, 80B, 80C, 80D (FIG. 3) mounted on the circuit board. In additional, light barricades 82 may be mounted on the circuit board to exclude ambient light from the detector 58 and to prevent improper optical communication or crosstalk between the emitter 56 and detector 58 in the housing 28. The emitter 56 and detector 58 are electrically connected to the signal processing circuitry, the details of which do not form a part of the present invention. Additional details concerning the operation of the signal processing circuitry and the interface with the controller and the wiper control system may be obtained from U.S. Pat. Nos. 4,620,141; 5,059,877; 5,239,244; and 5,262,640. To the extent any such details may be necessary to complete the descriptions and accounts necessary for purposes of the present application, they are deemed to be incorporated by reference herein.

When the moisture sensor is in operation, the controller (not shown) signals the emitter 56 which causes a light beam 60 to be emitted perpendicular to the circuit board 26. As shown in FIG. 3, the light beam is directed through the surface of the collimator lens 64 which reduces the divergence of the rays of the light beam 60. The rays of the light beam 60 travel through the clear material of the collimator lens 64 until striking the mirror surface 70, which reflects the light beam 60 approximately 60 degrees from the initial path of the light beam 60. The resulting optical axis 62 is at approximately a thirty degree angle with respect to the circuit board 26. The convex lens surface 72 of the collimator lens 64 collimates the light beam 60 for entry into the coupler 24.

The light beam 60 enters the coupler 24 at the surface 39 of detector prism 38. The surface 39 may include a convex curvature to ensure to ensure that the light beam 60 is fully collimated within the coupler 24. The detector prism 38 formed on the base 42 of the coupler 24 causes the light beam to be refracted approximately fifteen degrees. The light beam 60 is optically coupled into the interlayer 36 and then into the windshield 18 such that the light beam enters at an angle of approximately forty-five degrees.

The light beam 60 travels through the windshield 18, continuing at an angle of approximately forty-five degrees. At the outer surface 32 of the windshield 18, the beam is totally reflected and passes back through the windshield 18. If any moisture is present on the outer surface 32 of the windshield 18, a portion of the light beam 60 is not reflected and passes through the windshield 18. By detecting the light beam 60 reflected from the outer surface 32, the detector 58 of the moisture sensor 10 generates a control signal which is indicative of the amount of moisture on the outer surface 32 of the windshield 18.

The light beam 60 which is reflected from the outer surface 32 of the windshield 18 at approximately forty-five degree angle passes through the interlayer 36, the base 42 of the coupler 24, and the detector prism 40. The light beam 60 passes through the prism surface 41. The detector prism 40 is formed at an angle similar to the emitter prism 38 and results in the refraction of the of the light beam 60 by about fifteen degrees. The convex curvature of the prism surface 41 and of the convex lens surface 74 makes the light beam 60 slightly convergent. The light beam 60 passes through the collimator lens 66 until the light beam 60 is reflected from mirror surface 76 by total internal reflection. The light beam is reflected approximately sixty degrees by the mirror surface 76 such that the optical axis 62 of light beam 60 is once again normal to the circuit board 26.

The light beam passes through the detector collimator lens 66 and exits the lens 66 at planar surface 78. The planar surface 68 converges the light beam 60 to a point on the detector 58. Although the detector generally has the highest sensitivity when the light beams are perpendicular to the circuit board 26, any light beams 60 within the acceptance angle of the detector 58 will be detected. The detector 58 generates a control signal for the signal processing circuitry on the circuit board 26. The control signal is processed and transmitted to a controller for controlling the operation of the windshield wipers 20.

The preferred angle for the light beam 60 to enter the windshield 18 is forty-five degrees. In general, acceptable signals can be generated for an entry angle between forty and fifty degrees. As noted above, an angle above fifty degrees results in lost signals and an angle below forty degrees results in lost sensitivity. To obtain the forty-five degree angle when the light beam 60 initially starts out perpendicular to both the circuit board 26 and the windshield 18, the light beam is reflected at approximately sixty degrees and is refracted at approximately fifteen degrees. In general, the mirror surfaces 70, 76 reflect the light beam 60 to change the optical axis approximately sixty degrees, but acceptable reflection may occur in the range between fifty and seventy degrees. The prisms 38, 40 refract the light beam fifteen degrees, but the acceptable range is ten to twenty degrees. The important consideration is that the net effect of the reflection and refraction is a light beam 60 entering the windshield 18 at approximately forty-five degrees.

Ambient light often present a problem in moisture sensors 10 which use an optical detection system. Ambient light will generally enter the housing at an angle too steep to be sensed by the detector 58. In addition, light barricades 54,82 are formed in the housing and mounted on the circuit board to further exclude ambient light and prevent crosstalk between the emitter 56 and detector 58. The blocking grooves 44 built into the coupler 24 serve to trap crosstalk that may arise out of parasitic paths.

The convex lens surfaces 72, 74 on the lenses 64, 66 may be provided as aspheric surfaces. The use of aspheric surfaces reduces optical aberration, which tends to degrade the optical efficiency. The overall optical configuration of the emitter half of the sensor 10 and the detector half of the sensor 10 may be described as infinite conjugate ratio systems. This optical arrangement inherently provides low aberration, and thus the aspheric surfaces do not deviate greatly from truly spherical surfaces.

The optical axis 62 of light beam 60 strikes the prismatic surfaces 39, 41 of the coupler 24 at an oblique angle as opposed to deploying the coupling prisms with surfaces perpendicular to the optical axis. The oblique deployment of the prisms 38, 40 permits the optical axis 62 to be diverted to a direction perpendicular to the circuit board using a single reflector. This facilitates the use of a single circuit board 26 and a more shallow design of the coupler 24. The lenses 64, 66 perform several functions to help reduce the number of parts required in the sensor 10. A combination of the above factors permits a small and compact housing 28 to be used for the sensor 10.

Figure 4:
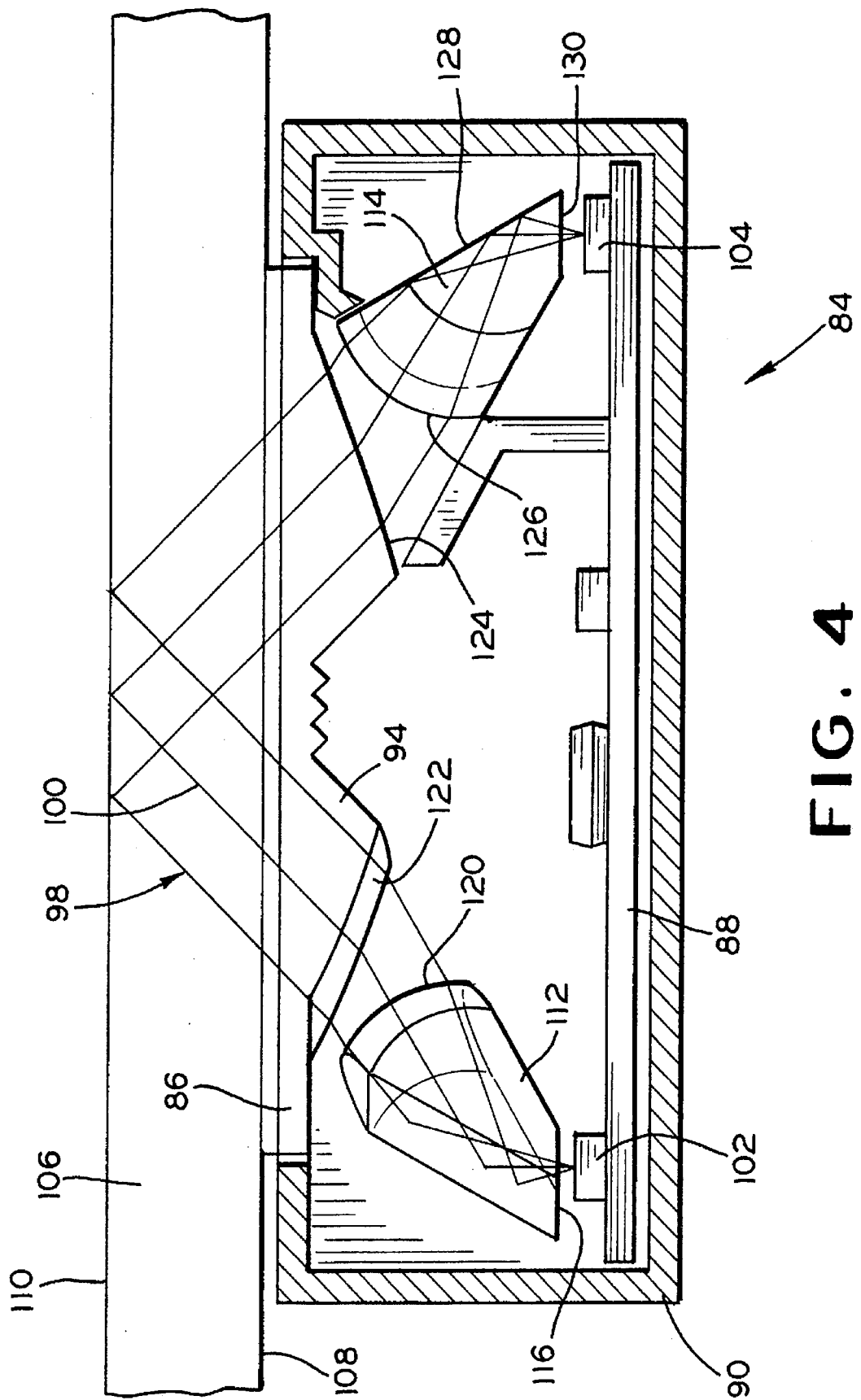
FIG. 4 is a transverse section view of an alternative embodiment of the moisture sensor having light beams from two emitters directed into a single detector.
Figure 5:
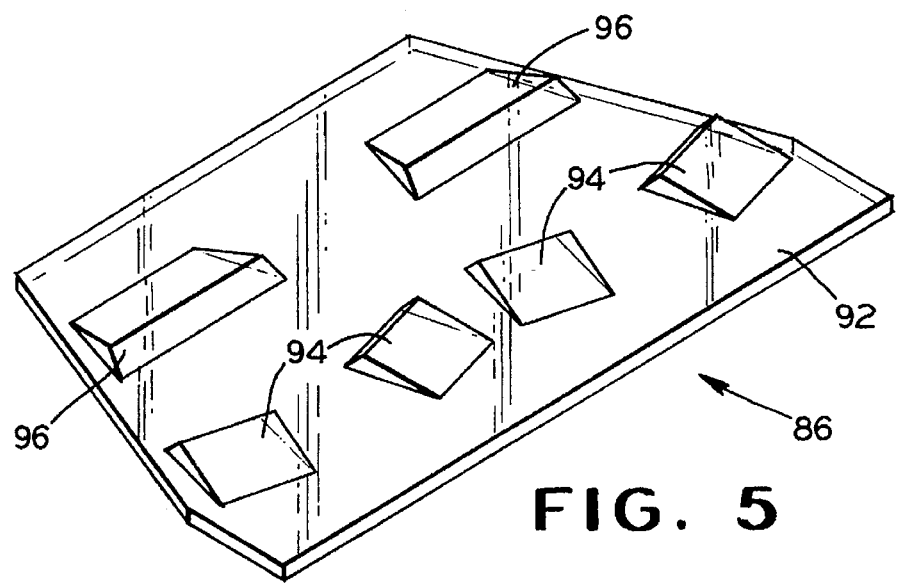
FIG. 5 is a perspective view of the prismatic coupler for the alterative embodiment shown in FIG. 4.
Figure 6:
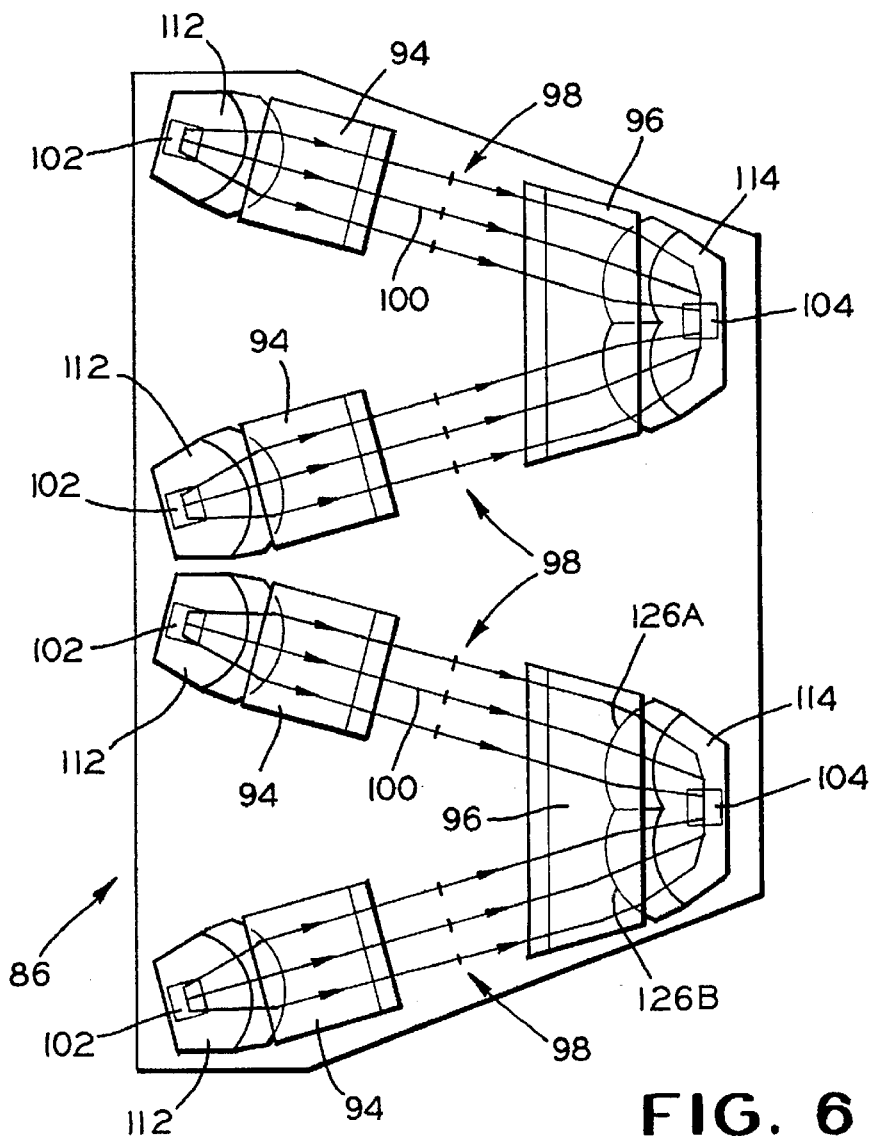
FIG. 6 is a schematic, top plan view of the prismatic coupler shown in FIG. 5 and including the positioning of the optical other optical elements mounted on the circuit board of the alterative embodiment to show the path of the light beams between the emitters and the detectors in the moisture sensor.

Referring now to FIGS. 4–6, an alternative embodiment of the present invention is provided with a different arrangement of the optical components. The main difference between the sensor 10 of the first embodiment and the sensor 84 of the alternative embodiment is the elimination of half the detectors by directing two light beams to the same detector.

In principle, a single detector may receive infrared radiation from several emitters. In the present invention, cost benefits can be obtained by combining two emitters with a single detector without adversely impacting the size or operating complexity of the moisture sensor 84. Although the discussion is directed to a sensor 84 with four emitters and two detectors, the sensor 84 may include any number of emitter-detector sets.

The moisture sensor 84 includes a detachable prismatic coupler 86, a circuit board 88, and a sensor housing 90. The sensor housing 90 has the same features as the housing 28 described above. The changes to the coupler 86 and to the arrangement of the optoelectronic components on the circuit board 88 will be highlighted below.

In FIG. 5, the coupler 86 includes a base 92 with four emitter prisms 94 and two detector prisms 96. The width of the detector prisms 96 has been increased to facilitate the receipt of two light beams 98 with optical axis 100 at one detector. The orientation of the prisms 94, 96 on the base 92 has been changed from the first embodiment to facilitate the transmittal of the light beams 98 between the emitters 102 and the detectors 104. The coupler 86 is mounted on the inner surface 108 of windshield 106 to detect moisture on the outer surface 110 of the windshield.

The collimator lenses 112 adjacent the emitter 102 are similar to the collimator lens 64 in the first embodiment. The collimator lens 114 adjacent the detector 104 has two distinct lens segments which are integrally formed to direct two light beams 98 into the single detector 104. The emitters 102, detectors 104, and collimator lenses 112, 114 are mounted on circuit board 88.

The collimator lens 112 is positioned above the emitter 102 on the initial optical axis 100 extending perpendicular from the emitter on the circuit board 88, which is similar to the first embodiment. To achieve proper alignment with the collimator lens 114, the collimator lens must also be rotated. The collimator lens 112 is rotated approximately ten to twelve degrees about the initial optical axis 100 extending perpendicular to the emitter 102. When the light beam 98 passes through the planar surface 116 and strikes the mirror surface 118, the light beam 98 is reflected sixty degrees so that the light beam 98 is at an angle of thirty degrees with respect to the circuit board 88 and also the inner surface 108 of the windshield 106. In addition, because of the rotation of the lens 112 on a vertical axis, the light beam 98 is also is also rotated in the plane of the windshield 106. The rotation of the collimator lens 112 and the path of the light beam 98 are shown in FIG. 6, in which only the optical system of the sensor 84 is illustrated.

After traveling through the collimator lens 112, the light beam 98 exits the lens 112 at the convex aspheric lens surface 120. As noted above, the rays of the light beam 98 are partially collimated. The light beam then passes through the prism surface 122 of emitter prism 94 on the coupler 86. This surface is also rotated approximately ten to twelve degrees in the plane of the windshield so that the optical axis 100 of the light beam 98 is not further rotated. The prism surface 122 is positioned such that the surface 122 is at an approximate angle of twenty-one degrees with respect to the inner surface 108 of the windshield 106.

The emitter prism 94 refracts the light beam 98 and optical axis 100 approximately fifteen degrees such that the light beam enters the windshield at the desired forty-five degree angle. A slight astigmatic curvature is included in the surface 122 of the prism 94 to fully collimate the light beam 98. The light beam 98 is coupled undeflected into the windshield 106 and is reflected by the outer surface 110 of the windshield 106.

The light beam 98 passes through the detector prism 96 on the coupler 86. The prism surface 124 has a common plane for two emitter optical paths. A slight convex curvature may be added to the prism surface 124, but the surface is reasonably flat. The surface 124 of the detector prism 96 is formed at an angle of approximately twenty-one degrees with respect to the inner surface 108 of the windshield 106. The light beam 96 leaves the windshield 106 at approximately forty-five degree angle and is refracted approximately fifteen degrees by detector prism 96 so that the light beam 98 is traveling at an angle of approximately thirty degrees with respect to the inner surface 108 of the windshield 106. Because of the orientation of the detector prism 96, the light beam 98 is rotated an additional five degrees in the plane of the windshield. After passing through the detector prism 96, the light beams 98 are at an angle of approximately sixteen degrees with respect to the longitudinal axis in the plane of the windshield.

After the detector prism 96, the light beam 98 enters the detector collimator lens 114 at the convex aspheric surface 126, which converges the light beam 98. The light beam strikes the mirror surface 128, which reflects the light beam 98 approximately sixty degrees such that light beam passes through planar surface 130 and is directed to the detector 104 on circuit board 88.

Because of the rotation of the light beam 94 within the plane of the windshield 106, the optical axis 100 of the light beam 98 after leaving the collimator lens 114 is not exactly perpendicular to the detector 104 on the circuit board 88. The light beam 98 will typically be approximately sixteen degrees from the axis extending from the detector 104 perpendicular to the circuit board 88. The detector 104 is mounted on the circuit board 88 such that the axis of highest sensitivity is perpendicular to the circuit board 88. Although the light beam 98 is directed to the detector 104 at an angle approximately sixteen degrees from vertical, the light beam 98 strikes the detector 104 well within the acceptance angle of the detector 104.

FIG. 6 shows the configuration of the optical components and the path of the light beam 98 with optical axis 100 when two emitters 102 are directed to a single detector 104. The detector collimated lens 114 has the appropriate convex surface 126, mirror surface 128, and planar surface to accommodate light beams 98 form two emitters 102. The convex surface 126 of the detector collimated lens 114 is splayed apart to provide two distinct surfaces 126A, 126B for converging the light beams 98.

FIG. 6 also shows the slight rotation of the beams 98 within the plane of the windshield 106. The light beams from the two emitters form a V-type arrangement. When two sets are used in a single sensor 84, the third and fourth emitters 102 and the second detector 104 are positioned as shown. The housing 90 may be reduced in size because the optical configuration permits to light beams to share common active optical elements. The mirror surface 128 and planar surface 130 of the detector collimated lens 114 are common to two optical paths. This optical technique of angular spectrum multiplexing saves space and reduces the cost of the sensor 84. The mounting of the circuit board 88 parallel to the inner surface 108 of the windshield 106 provides significant space and cost reduction in the manufacturing of the sensor 84.

In the sensor 84 (and also in sensor 10), the total focal power of all of the optical surfaces which the light beam 98 encounters before it is coupled to the windshield 106 must be sufficient to collimate the light beam 106. The majority of the focal power is placed at the convex lens surface 20 of the collimator lens 112, and a lessor amount is placed at the prism surface 122 of the coupler 86. The focal power may be distributed differently by adjusting the curvature of the surfaces so long as the changes to the prism surface 122 do not adversely effect the necessary refraction of the light beam 98.

One option to adjust the focal power is to add focal power earlier in the optical path by making the planar surface 116 convex. It is also possible to add focal power to the mirror surface 118 by making the mirror surface 118 a parabolic section with the focal point of the parabola located at the emitter 102. The prism surface 122 may be implemented as a segmented surface, or Fresnel lens, at the expense of optical efficiency. A similar redistribution of focal power may be utilized on the detector optics of the sensors 10, 84. However, in general, it is preferable to place the focal power at the end of the optical path from the emitter 102 to the windshield so as to lengthen the focal length of the optics. Increasing the focal length results in fewer rays of the light beam 98 to missing the detector prism 96. In addition, the longer focal lengths permit less critical tolerance in many of the parts.

In addition to the front windshield of a motor vehicle, the moisture sensor of the present invention can also be used on other glass surfaces for the detection of moisture.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A moisture sensor for mounting on a surface of a sheet of glass to detect moisture on an opposite surface of the sheet of glass, said moisture sensor comprising:

a) a coupler for mounting on an inner surface of a sheet of glass, said coupler including a pair of prismatic refracting regions in spaced apart relationship;

b) a housing secured to said coupler;

c) a planar circuit board secured in said housing and having a device surface which is positioned generally parallel to the inner surface of the sheet of glass;

d) an emitter mounted on the device surface, said emitter emitting light beams with an optical axis approximately perpendicular to the device surface of said circuit board;

e) an emitter lens mounted in said housing and positioned between said emitter and a first prismatic region of said coupler, said emitter lens including a reflection surface;

f) a detector mounted on the device surface for detecting light beams striking the detector at an angle within an acceptance angle of said detector, and for generating control signals in response to the light beams; and g) a detector lens having a reflection surface, said detector lens mounted in said housing and positioned between said detector and a second prismatic region of said coupler; and said emitter lens, said coupler with prismatic refracting regions, and said detector lens positioned to form an optical path from said emitter to an outer surface of said glass, and back to said detector such that the light beams are emitted at an angle approximately perpendicular to said circuit board, are directed into and reflected from the sheet of glass at an angle between forty and fifty degrees, and are received at the detector at an angle within the acceptance angle of said detector.

2. The moisture sensor defined in claim 1, including a signal processing circuit mounted on said circuit board and connected to said emitter and said detector for controlling the light beams emitted by the emitter and for processing the control signals from said detector.

3. The moisture sensor defined in claim 1, including a plurality of emitters, emitter lenses, detectors, and detector lenses mounted on said circuit board and a corresponding plurality of prismatic refracting regions formed in said coupler, said emitters, emitter lenses, detectors, detector lenses, and prismatic regions being positioned to form a plurality of optical paths in which light beams are emitted at an angle approximately perpendicular to said circuit board, are directed into and reflected from the sheet of glass at an angle between forty and fifty degrees, and are received at the detector at an angle within the acceptance angle of said detector.

4. The moisture sensor defined in claim 1, wherein the prismatic refracting regions in said coupler include a convex surface for collimating the light beams.

5. The moisture sensor defined in claim 1, wherein said emitter lens and said detector lens each include a convex surface for collimating the light beams.

6. The moisture sensor defined in claim 5, wherein the convex surfaces are aspheric surfaces.

7. The moisture sensor defined in claim 1, wherein the combined reflection of the light beams by the emitter lens and refraction of the light beams by the first prismatic region deflects the light beams in the range between forty and fifty degrees, and the combined refraction of the light beams by the second prismatic region and reflection of the light beams by the detector lens deflects the light beams in the range between forty and fifty degrees.

8. The moisture sensor defined in claim 7, wherein the light beams are deflected approximately forty-five degrees by reflection in the emitter lens and refraction in the first prismatic region, and wherein the light beams are deflected approximately forty-five degrees by refraction in the second prismatic region and reflection in the detector lens.

9. The moisture sensor defined in claim 8, wherein the light beams are reflected approximately sixty degrees by said emitter lens and refracted approximately fifteen degrees by the first prismatic region, and wherein the light beams are refracted approximately fifteen degrees by the second prismatic region and reflected approximately sixty degrees by said detector lens.

10. The moisture sensor defined in claim 1, wherein said coupler has a thickness of 5 mm or less.

11. The moisture sensor defined in claim 1, wherein said emitter and said detector are surface mounted devices.

12. The moisture sensor defined in claim 1, wherein the prismatic refracting regions on said coupler include a surface formed at an angle of approximately twenty-one degrees with respect to the inner surface of the sheet of glass.

13. The moisture sensor defined in claim 1, wherein said coupler includes light blocking grooves.

14. The moisture sensor defined in claim 1, including light blockers mounted on said circuit board and positioned in proximity to said detector.

15. The moisture sensor defined in claim 1, wherein the light beams are received at said detector at an angle approximately perpendicular to said circuit board.

16. A moisture sensor for mounting on a surface of a sheet of glass to detect moisture on an opposite surface of the sheet of glass, said moisture sensor comprising:

a) a coupler for mounting on an inner surface of a sheet of glass, said coupler including three prismatic refracting regions in spaced apart relationship;

b) a housing secured to said coupler;

c) a planar circuit board secured in said housing and having a device surface which is positioned generally parallel to the inner surface of the sheet of glass;

d) a first emitter and a second emitter mounted on the device surface in spaced apart relationship, said emitters emitting light beams with an optical axis approximately perpendicular to the device surface of said circuit board;

e) a first emitter lens mounted in said housing and positioned between said first emitter and a first prismatic region, and a second emitter lens mounted in said housing and positioned between said second emitter and a second prismatic region, said emitter lenses including a reflection surface;

f) a detector mounted on the device surface for detecting light beams striking the detector at an angle within an acceptance angle of said detector, and for generating control signals in response to the light beams;

g) a detector lens having a reflection surface, said detector lens mounted in said housing and positioned between said detector and a third prismatic region of said coupler; and said emitter lenses, said coupler with prismatic refracting regions, and said detector lens positioned to form a first optical path from said first emitter to an outer surface of said glass and back to said detector, and a second optical path from said second emitter to an outer surface of said glass and back to said detector, such that the light beams from said first and second emitters are emitted at an angle approximately perpendicular to said circuit board, are directed into and reflected from the sheet of glass at an angle between forty and fifty degrees, and are received at the detector at an angle within the acceptance angle of said detector.

17. The moisture sensor defined in claim 16, including a signal processing circuit mounted on said circuit board and connected to said emitters and said detector for controlling the light beams emitted by the emitters and for processing the control signals from said detector.

18. The moisture sensor defined in claim 16, wherein the light beams are received at said detector at an angle of approximately sixteen degrees with respect to a perpendicular axis extending from said detector on said circuit board.

19. The moisture sensor defined in claim 16, wherein the light beams are reflected approximately sixty degrees by said emitter lenses and refracted approximately fifteen degrees by the first prismatic region, and wherein the light beams are refracted approximately fifteen degrees by the second prismatic region and reflected approximately sixty degrees by said detector lens, and wherein the light beams are rotated within a plane of the windshield approximately eleven degrees by said emitter lenses and approximately five degrees by the third prismatic region of said coupler.

20. The moisture sensor defined in claim 16, including at least one additional optical set mounted on said circuit board, said optical sets comprising at least two emitters, a equivalent number of emitter lenses, a detector, and a detector lens, and a including a corresponding plurality of prismatic refracting regions formed in said coupler such that said emitters, emitter lenses, detectors, detector lenses, and prismatic regions being positioned to form a plurality of optical paths in which light beams are emitted at an angle approximately perpendicular to said circuit board, are directed into and reflected from the sheet of glass at an angle between forty and fifty degrees, and are received at the detectors at an angle within the acceptance angle of said detectors.

* * * * *